United States Patent
Au-Young et al.

(12) 
(10) Patent No.: US 6,309,821 B1
(45) Date of Patent: *Oct. 30, 2001

(54) DNA ENCODING A PAC10 HUMAN HOMOLOG

(75) Inventors: Janice Au-Young, Berkley; Richard D. Goold, San Francisco, both of CA (US)

(73) Assignee: Incyte Genomics, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/648,736

(22) Filed: May 16, 1996

(51) Int. Cl.$^7$ ............................. C12Q 1/68; C12P 19/34
(52) U.S. Cl. ............................................. 435/6; 435/91.2
(58) Field of Search ..................... 435/6, 91.2; 536/23.1, 536/22.1, 24.3, 24.31, 24.33

(56) References Cited

PUBLICATIONS

Hwang, D.M. et al., (GI 828841) GenBank Sequence Database (Accession R58783), National Center for Biotechnology Information, National Library of Medicine, Bethesda, Maryland, 20894.

Tsuchiya, H et al., "Identification of a Novel Protein (VBP–1) Binding to the von Hippel–Lindau (VHL) Tumor Suppressor Gene Product" *Cancer Research* 56:2881–2885 (1996).

Lillie, S.H., et al., "Suppression of a myosin defect by a kinesin–related gene" *Nature*, 356:258–361 (1992).

Aizawa, H., et al., "Kinesin Family in Murine Central Nervous System" *J. Cell Biol.*, 119(5):1287–1296 (1992).

"Harrison's Principles of Internal Medicine" 13 edition, publisher McGraw–Hill, ed. Isselbacher et al., p. 2387.

Dahl, N., et al., "Myotubular Myopathy in a Girl with a Deletion at Xq27–q28 and Unbalanced X Inactivation Assigns the MTMI Gene to a 600–kb Region" *Am. J. Hum. Genet.* 56:1108–1115 (1995).

Geiser, J.R., et al., (GI 902026), GenBank Sequence Database (Accession 902026), National Center for Biotechnology Information, National Library of Medicine, Bethesda, Maryland 20894.

Gentles, S., et al., (GI 1177665), GenBank Sequence Database (Accession 1177665), National Center for Biotechnology Information, National Library of Medicine, Bethesda, Maryland 20894.

Julius, D., et al., "The 5HT2 receptor defines a family of structurally distinct but functionally conserved serotonin receptors" *Proc. Natl. Acad. Sci.*, 87:928–932 (1990).

Saltzman, A.G., et al., "Cloning of the Human Serotonin 5–HT2 and 5–HT1C Receptor Subtypes" *Biochem. Biophys. Res. Commun.*, 181:1469–1478 (1991).

*Primary Examiner*—Eggerton A. Campbell
(74) *Attorney, Agent, or Firm*—Incyte Genomics, Inc.

(57) ABSTRACT

The present invention provides nucleotide and amino acid sequences for a novel PAC10 human homolog. The present invention also provides for antisense molecules, diagnostic molecules, genetically engineered expression vectors and host cells for the production of purified PAC10 homologs; antibodies, agonists, antagonists and inhibitors of the PAC10 human homolog; and pharmaceutical compositions and methods of treatment based on the polypeptide, its antibodies, ntagonists and inhibitors. The invention further provides diagnostic and theapeutic compositions for the detection and treatment of X-linked congenital abnormalities, such as centronuclear myopathy.

7 Claims, 13 Drawing Sheets

```
                 9            18           27           36           45           54
5' TNC CCA AGN AGN CCA TNC CTT TGG ACA ACN AGC GCA AAT NAT TTA CAG CAT CAA 63           72           81           90           99          108
   AAT GGT TGC AAA TCC TGG NCA AAT GGG NCT GCA AAA CAG CAG CTT TGT TGG AAG 117          126          135          144          153          162
   CCT TNT TTT NTA ATT CCA TGG CAT CAG AAG ACC CTT TAA TGA GGC ANA TNA GTT 171          180          189          198          207          216
   CAT CAA NNA NAA TNC CCC TGG TGG GCA NAA GAC TAA CTN AGT NAC CAT TGC ACC 225          234          243          252          261          270
   CAG ACG CCT GGG TGC ATC ACA GCA TTN CTG CAT CAA AAA CAT CAA TGT NAT NGT 279          288          297          306          315          324
   TNC ATN CCC CTG TGA GTN AAA AAT NAC ACT CAC ACA TGT TTT GTC ACT GTN ATT 333          342          351          360          369          378
   NCT GNA ANT NAA AAC ATG CNG CNA AAA NAA AAA AAA AAA AAA AAA AAC GCA GGG 387          396          405          414          423          432
   GNC GTN ACC ATG CGC KCT CGC ATC CCC AAG ATG GCG GCC GTT AAG GAC AGT TGT 441          450          459          468          477          486
   GGC AAA GGA GAA ATG GCC ACA GGG AAT GGG CGG CGG CTC CAC CTG GGG ATT CCT
                           M    A    T    G    N    G    R    R    L    H    L    G    I    P 495          504          513          522          531          540
   GAG GCC GTG TTT GTG GAA GAT GTA GAT TCC TTC ATG AAA CAG CCT GGG AAT GAG
    E    A    V    F    V    E    D    V    D    S    F    M    K    Q    P    G    N    E 549          558          567          576          585          594
   ACT GCA GAT ACA GTA TTA AAG AAG CTG GAT GAA CAG TAC CAG AAG TAT AAG TTT
    T    A    D    T    V    L    K    K    L    D    E    Q    Y    Q    K    Y    K    F 603          612          621          630          639          648
   ATG GAA CTC AAC CTT GCT CAA AAG AAA AGA AGG CTA AAA GGT CAG ATT CCT GAA
    M    E    L    N    L    A    Q    K    K    R    R    L    K    G    Q    I    P    E 657          666          675          684          693          702
   ATT AAA CAG ACT TTG GAA ATT CTA AAA TAC ATG CAG AAG AAA AAA GAG TCC ACC
    I    K    Q    T    L    E    I    L    K    Y    M    Q    K    K    K    E    S    T 711          720          729          738          747          756
   AAC TCA ATG GAG ACC AGA TTC TTG CTG GCA GAT AAC CTG TAT TGC AAA GCT TCA
    N    S    M    E    T    R    F    L    L    A    D    N    L    Y    C    K    A    S 765          774          783          792          801          810
   GTT CCT CCT ACC GAT AAA GTG TGT CTG TGG TTG GGG GCT AAT GTA ATG CTT GAA
    V    P    P    T    D    K    V    C    L    W    L    G    A    N    V    M    L    E 819          828          837          846          855          864
   TAT GAT ATT GAT GAA GCT CAG GCA TTG TTG GAA AAG AAT TTA TCG ACT GCC ACA
    Y    D    I    D    E    A    Q    A    L    L    E    K    N    L    S    T    A    T
```

FIGURE 1A

```
                873              882              891              900              909              918
        AAG AAT CTT GAT TCC CTG GAG GAA GAC CTT GAC TTT CTT CGA GAT CAA TTT ACT
         K   N   L   D   S   L   E   E   D   L   D   F   L   R   D   Q   F   T 927              936              945              954              963              972
        ACC ACA GAA GTC AAT ATG GCC AGG GTT TAT AAT TGG GAT GTA AAA AGA AGA AAC
         T   T   E   V   N   M   A   R   V   Y   N   W   D   V   K   R   R   N 981              990              999             1008             1017             1026
        AAG GAT GAC TCT ACC AAG AAC AAA GCA TAA TGC TGG CAA TTA AAA ATG TGG TTT
         K   D   D   S   T   K   N   K   A 1035             1044             1053             1062             1071             1080
        AGT TTT CCA AAC ATG TTA TCT TAA ATA CCC CTT TAT CCT TAC AGG TTG ACA TAA 1089             1098             1107             1116             1125             1134
        CTT TGA ATG TTT TAA CAG CAA GAA TTT TAA GAA AAG ATA AAC ACC ATT TTA TTT 1143             1152             1161             1170             1179             1188
        ATT TAT AAA AAC AAA ATT AGT TTC AAA TAT TTT TGA CAT TGT GAT TTT TTT TTC 1197             1206             1215             1224             1233             1242
        CAC ATT TCT CAG CAA AGC TAA TGG TAT TTT AAT CAT TAT TTT TGC CTG TCA TAA 1251             1260             1269             1278             1287             1296
        GGA AAC TCT TAG CTG AAA TGG CCG NAA ACT GTG NGN CAT GCT ATG GAA GCT GAA 1305             1314
        TGN CGG ACG NTA GCA CAG  3'
```

FIGURE 1B

```
         M. . . . . . . . . .G I P . A . F . E . . . . . . K .  Consensus #1
         |―――――――――――――|―――――――――――――|―――――――――――――|
                      10            20            30
  1    M D T L F N S T E K N A R G I P Q A P F I E N V N E I I K D  Saccharomyces Pac10p
  1    M S S - - S N P R - - - - G I P P A Q F F E - - - - - F K E  S. pombe gi1177665
  1    M A T - - G N G R R L H L G I P E A V F V E D V D S F M K Q  New 41400

. . . . . . . . . . . K . . E . . . . K Y K F M . . . . . . . Consensus #1
         |―――――――――――――|―――――――――――――|―――――――――――――|
                      40            50            60
 31    P S - - D F E L C F N K F Q E R L S K Y K F M Q E S K L A T  Saccharomyces Pac10p
 20    L S M E E A Q G H L E K F Q E A I A K Y K F M E T S V V R R  S. pombe gi1177665
 29    P G N E T A D T V L K K L D E Q Y Q K Y K F M E L N L A Q K  New 41400

. . . L . . . I P . . . . T L . . . . . . . . . . . . . . . Consensus #1
         |―――――――――――――|―――――――――――――|―――――――――――――|
                      70            80            90
 59    I K Q L K T R I P D L E N T L K I C Q S L R N H S D E G D E  Saccharomyces Pac10p
 50    V A S L D D K I P D I R K T L Q S V Q F L K E R - - - - Q G  S. pombe gi1177665
 59    K R R L K G Q I P E I K Q T L E I L K Y M Q K K - - - - K E  New 41400

. . . . . . . . . L . D . L . . K A . V . . . . . . . . . . Consensus #1
         |―――――――――――――|―――――――――――――|―――――――――――――|
                     100           110           120
 89    S D E P I L L H Y Q L N D T L Y T K A Q V D I P E D R A D L  Saccharomyces Pac10p
 76    - - D S F T V T Y E L N D T L N A K A E V E A K D - - - - -  S. pombe gi1177665
 85    S T N S M E T R F L L A D N L Y C K A S V P P T D - - - - -  New 41400

. V . L W L G A . V M L E Y . . . E A . . L L . . . L . . . Consensus #1
         |―――――――――――――|―――――――――――――|―――――――――――――|
                     130           140           150
119    K V G L W L G A D V M L E Y P I D E A I E L L K K K L A D S  Saccharomyces Pac10p
 99    N V Y L W L G A N V M L E Y T V E E A E A L L T Q K L N S A  S. pombe gi1177665
110    K V C L W L G A N V M L E Y D I D E A Q A L L E K N L S T A  New 41400

. . . L . . . . E D . . F L R . . . . T T . E V N . A R . Y N Consensus #1
         |―――――――――――――|―――――――――――――|―――――――――――――|
                     160           170           180
149    E Q S L T V S T E D V E F L R E N I T T M E V N C A R L Y N  Saccharomyces Pac10p
129    E E T L K A C K E D L E F L R A Q V T T M E V N T A R V Y N  S. pombe gi1177665
140    T K N L D S L E E D L D F L R D Q F T T T E V N M A R V Y N  New 41400

. . V . . R . . . . . . . . . . . . . K .        Consensus #1
         |―――――――――――――|―――――――――――――|
                     190           200
179    W D V Q R R Q D L K Q A Q E G T K N L K I   Saccharomyces Pac10p
159    Y T V L L R K K - - - - T - - - - - - K M   S. pombe gi1177665
170    W D V K R R N K - - - - D D S T K N - K A   New 41400

Consensus 'Consensus #1': When all match the residue of the Consensus show the
residue of the Consensus, otherwise show '.'.

Decoration 'Decoration #1': Box residues that match the consensus named
'Consensus #1' exactly.
```

FIGURE 2

>gi|177776|gp|M86841|HUM5HT2A_1 serotonin receptor [Homo sapiens]
    Length = 456

Plus Strand HSPs:

Score = 68 (31.4 bits), Expect = 0.021, P = 0.021
  Identities = 13/43 (30%), Positives = 22/43 (51%), Frame = +1

Query:     31 NLSTATKNLDSLEEDLDFLRDQFTTTEVNMARVYNWDVKRRNK 159
              +LS+ T +L   L +D     + F + E N +  +NW V   N+
Sbjct:      2 SLSSTTNSLMQLNDDTRLYSNDFNSGEANTSDAFNWTVDSENR 44

>gi|36431|gp|X57830|HSSERR52_1 serotonin 5-HT2 receptor [Homo sapiens]
    Length = 471

Plus Strand HSPs:

Score = 68 (31.4 bits), Expect = 0.021, P = 0.021
  Identities = 13/43 (30%), Positives = 22/43 (51%), Frame = +1

Query:     31 NLSTATKNLDSLEEDLDFLRDQFTTTEVNMARVYNWDVKRRNK 159
              +LS+ T +L   L +D     + F + E N +  +NW V   N+
Sbjct:     10 SLSSTTNSLMQLNDDTRLYSNDFNSGEANTSDAFNWTVDSENR 52

FIGURE 6

41400 is mapped on chromosome Xq27-28

```
                                   260        270        280        290        300        310        320        330        340
                                    |          |          |          |          |          |          |          |          |
40735.Assemblage.8                 CAATGTnAtnGTTnCATnCCCCTGTGAGTnAAAAATnACACTCACACATGTTTTGTCACTGTnATTnCTGnAAnTnAAAACATGCn
                                                                       .          .          .          .          .

12844-21m13              <-        CAATGTNATNGTTNCATnCCCCTGTGAGTNAAAAATNACACTCACACATGTTTTGTCACTGTNATTNCTGNAANTNAAACATGCN 350        360        370        380        390        400        410        420        430
                                    |          |          |          |          |          |          |          |          |
40735.Assemblage.8                 GCnAAAAnAAAAAAAAAAAAAAAAAAAACGCAGGGnCGTnACCATGCgCkCTC~GCA~~TcCCCAAGATGGCGGCCGTTAAGGACA
                                           .          .                                   .          ...

12844-21m13              <-        GCNAAAANAAAAAAAAAAAAAAAAAAAACGCAGGGGNCGTNACCATGC~CTCTCNGCA
826058                   -^                                                                CGCGCTC-GCA--TCCCCAAGATGGCGGCCGTTAAGGACA
134937                   -^                                                                 CTC-GCA--TCCCCAAGATGGCGGCCGTTAAGGACA
490767                   -^                                                                  C-GCA--TCCCCAAGATGGCGGCCGTTAAGGACA
263915                   -^                                                                         GCANGTAGCCAANATGGGCGCCGTTAAGGACA
495844                   -^                                                                              CCAAGATGGCGGCCGTTAAGGACA 440        450        460        470        480        490        500        510
                                    |          |          |          |          |          |          |          |
40735.Assemblage.8                 GTTGTGGCAAAGGAGAAATGGCCACAGGGAATGGGCGGCGCTCCACCTGGGATTCCTGAGGCCGTGTTTGTGGAAGATGTAGAT 826058                   -^        GTTGTGGCAAAGGAGAAATGGCCACAGGGAATGGGCGGCGCTCCACCTGGGATTCCTGAGGCCGTGTTTGTGGAAGATGTAGAT
134937                   -^        GTTGTGGCAANGGAGAAATGGCCACAGGGAATNGCCNCGCGGCGCTCCACCTGGGAATTCCTNCNCGCCGTGTTNTGGAAGATNTAGNT
490767                   -^        GTTGTGGCAAAGGAGAAATGGCCACAGGGAATGGCCGGCGCTCCACCTGGGATTCCTGAGGCCGTGTTGTGGAAGATGTAGAT
263915                   -^        GTTGTGGCAAAGGAGAAATGGCCACAGGGAATGGCCGGCGCTCCACCTGGGATTCCTGAGGCCGTGTTGTGGAAGATGTAGAT
495844                   -^        GTTGTGGCAAAGGAGAAATGGCCACAGGGAATGGCCGGCGCTCCACCTGGGATTCCTGAGGCCGTGTTGTGGAAGATGTAGAT
```

DNA ENCODING A PAC10 HUMAN HOMOLOG

FIELD OF THE INVENTION

The present invention relates generally to the field of molecular biology and particularly novel polynucleotide and amino acid sequences for a human homolog of the Pac10 gene of Saccharomyces cerevisiae. The present invention provides compositions and methods for the diagnosis and treatment of disease states such as X-linked centronuclear myopathy, schizophrenia and mental retardation.

BACKGROUND OF THE INVENTION

Motor proteins in cells include myosin, which is actin-based, and kinesin, dynein and dynamin, which are microtubule-based (Lillie 1992, Nature 356:358–361). Kinesin has been identified as a transporter of membranous organelles in mammalian neurons. Genes related to kinesin heavy chain have been identified in Schizosaccharomyces pombe and Saccharomyces cerevisiae. Most of the members of the kinesin family are implicated in mechanisms of mitosis or meiosis (Aizawa 1992, J. Cell. Biol. 119:1287–1296).

The Pac10 gene of Saccharomyces cerevisiae, which encodes the heavy chain of members of the kinesin family, is required for viability in the absence of the kinesin-related CIN8 mitotic motor. If deleted with CIN8, an associated family member, the Pac 10/CIN8 double mutation is lethal and presumably prevents separation of the spindle pole bodies (Geiser, J R and Hoyt M A, unpublished data).

Centronuclear myopathy is an X-inked congenital myopathy (MTMI) that has been localized to Xq28 (*Harrison's Principles of Internal Medicine,* 13 edition, ed. Isselbacher et al., publisher McGraw-Hill, New York, pg 2387). Dahl et al. (1995 Am. J. Hum. Genet. 56:1108–1115) report that a young girl with a clinically moderate form of myotubular myopathy and associated mental retardation was found to carry a cytogenetically detectable deletion in Xq27-q28. Positional cloning of the MTMI locus has been refined to a 600 kb region between the DX5304 and DX5497 markers. Other diseases linked to the Xp27-q28 locus include schizophrenia, X-linked mental retardation associated with Fragile Site FRAXE and anophthalmos.

The neonatal form of centronuclear myopathy is X-linked and presents with severe hypotonia and weakness at birth. Patients may require respiratory assistance and a feeding tube due to swallowing difficulties. This form of the disease is often fatal. The early childhood form presents without difficulty at birth, but motor milestones, such as walking, running and stair climbing, are delayed. In this form the disease may be static or may progress to weakness. A rare form of the disease has an onset in the second or third decade. The early childhood and adult forms appear to have autosomal dominant or recessive inheritance patterns. Patients with the neonatal form of centronuclear myopathy require carefull management for respiratory support and gastric feeding, and patients with the early childhood disorder often require ambulatory aids and orthotic devices and less often wheelchairs.

Schizophrenic disorders are serious mental illnesses that cause significant social, vocational, and personal disability. In the United States there are about 2 million affected individuals and these individuals account for an estimated loss of 20 billion dollars of lost productivity per year (Harrison's Principles of Internal Medicine supra pg. 2414–2415). X chromosome linked mental retardation is the second most common genetic cause of mental retardation (after Down's syndrome) (Pathophysiology, 2nd Edition, Editors McCance et al., publisher, Mosby, St. Louis pg. 1420). Anopthalmos is a developmental defect characterized by mental retardation and a complete absence of the eyes or by the presence of vestigal eyes.

In view of the severity of the diseases associated with the Xq27-q28 locus, including centronuclear myopathy, myotubular myopathy, schizophrenia, X-linked mental retardation associated with Fragile Site FRAXE and anophthalmos, it would be advantageous to provide an early and accurate method for the detection of such diseases. It would also be advantageous to provide therapeutic compositions and methods for prevention and treatment of such diseases.

SUMMARY

Because the present invention relates to novel nucleotide and amino acid sequences disclosed herein for a PAC 10 human homolog and the nucleotide sequence has been mapped to the Xq27-q28 locus, the present invention also relates to the use of the PAC 10 human homolog in the diagnosis, prevention and treatment of diseases associated with the Xq27-q28 locus, such as centronuclear myopathy, myotubular myopathy, schizophrenia, X-linked mental retardation associated with Fragile Site FRAXE and anophthalmos.

The nucleotide sequence for Incyte clone 41400, encoding the PACIO human homolog, was initially found among the nucleic acid sequences of a cDNA library made from hybrid cells of T-B lymphoblasts from a leukemic cell line. Clone number 41400 was found to have amino acid homology to the Pac10 gene of Saccharomyces cerevisiae which encodes the heavy chain members of the kinesin family that are implicated in mechanisms of mitosis or meiosis. Based upon the results of a BLAST search (which stands for Basic Local Alignment Search Tool (Altschul S F (1993) J Mol Evol 36:290–300; Altschul, S F et al (1990) J Mol Biol 215:403–10)), the PAC10 human homolog appears to have a more distant relationship to the beta cardiac myosin heavy chain (Oryctolagus cuniculus) and the neuronal myosin heavy chain (Rattus rattus). The Pac10 human homolog also shares some nucleotide sequence homology with the serotonin receptors, NCBI Entrez accession numbers GI 177776 and GI 36431.

The present invention is therefore based on the discovery of a novel cytoskeletal gene which maps to the locus Xq27-28 that may be associated with disease states, such as centronuclear myopathy, myotubular myopathy, schizophrenia, X-linked mental retardation associated with Fragile Site FRAXE and anophthalmos. The PAC10 human homolog and nucleotide sequences that encode it and oligonucleotides, peptide nucleic acid (PNA), fragments, portions or antisense molecules thereof, provide the basis for diagnostic methods for the detection and/or quantitation of the Pac10 human homolog that is associated with myopathy and X-linked mental retardation. For example, the nucleotide sequence disclosed herein, which encodes the PAC10 human homolog, or fragments thereof, may be used in hybridization assays of biopsied cells or tissues or bodily fluids, such as amniotic fluid to detect the nucleic acid which may be associated with such disease states.

An abnormal level of the Pac10 human homolog nucleotide sequences or an abnormal transcript size in a biological sample may be characteristic of a regulatory state in which the molecules are over-expressed or under-expressed. Nucleotide sequences encoding the PAC 10 human homolog provide the basis for probes which can be used diagnostically to detect chromosomal aberrations such as deletions, mutations or chromosomal translocations in the gene encoding the molecule. Gene expression may be altered in such disease states or there may be a chromosomal aberration present in the region of the gene encoding the molecule.

The present invention also relates, in part, to expression vectors and genetically engineered host cells comprising nucleotide sequences encoding the Pac10 human homolog for in vitro or in vivo production of the nucleotide sequences.

Additionally, the present invention relates to the use of the PAC10 human homolog polypeptide, or fragment or variant thereof, to produce antibodies and to screen for antagonists or inhibitors of the PAC10 human homolog which can be used diagnostically to detect and quantitate protein levels in disease states.

Peptides or small molecules capable of modulating PAC10 human homolog activity will provide the basis for pharmaceutical compositions for the treatment of disease states associated with the Xq27-28 locus.

The invention further provides diagnostic assays and kits for the detection of the PAC 10 human homolog in cells and tissues comprising the PAC10 human homolog which may be used as a positive control, and anti-PAC10 antibodies. Such antibodies may be used in solution-based, membrane-based, or tissue-based technologies to detect any disease state or condition related to the expression of protein or expression of deletions or variants thereof.

The present invention also provides diagnostic assays and kits that comprise Pac10 human homolog nucleic acid probes for the detection of mutations, deletions or translocations in the Pac10 human homolog gene. Such probes can be used in hybridization assays, including PCR based techniques, to detect a disease state or condition associated with the Pac10 gene.

DESCRIPTION OF THE FIGURES

FIGS. 1A and 1B display the polynucleotide (SEQ ID NO:1) and deduced amino acid (SEQ ID NO:2) sequence for the PAC10 human homolog.

FIG. 2 displays the amino acid alignment of the PAC10 human homolog with the *Saccharomyces cerevisiae* Pac10 (GenBank 902026) and the *Schizosaccharomyces pombe* protein SPAC3H8.07c (GenBank 1177665). Sequences shown in this figure were produced using the multisequence alignment program of DNASTAR software (DNASTAR Inc, Madison Wis.).

FIG. 6 displays the amino acid alignment of Incyte clone 41400 with the Serotonin receptors, GI accession numbers gi 177776 and gi 36431.

FIGS. 8A, 8B, 8C, 8D, and 8E illustrates the assembly of partial cDNA sequences into a full length polynucleotide sequence encoding the PAC10 human homolog.

DETAILED DESCRIPTION

Figure 3:
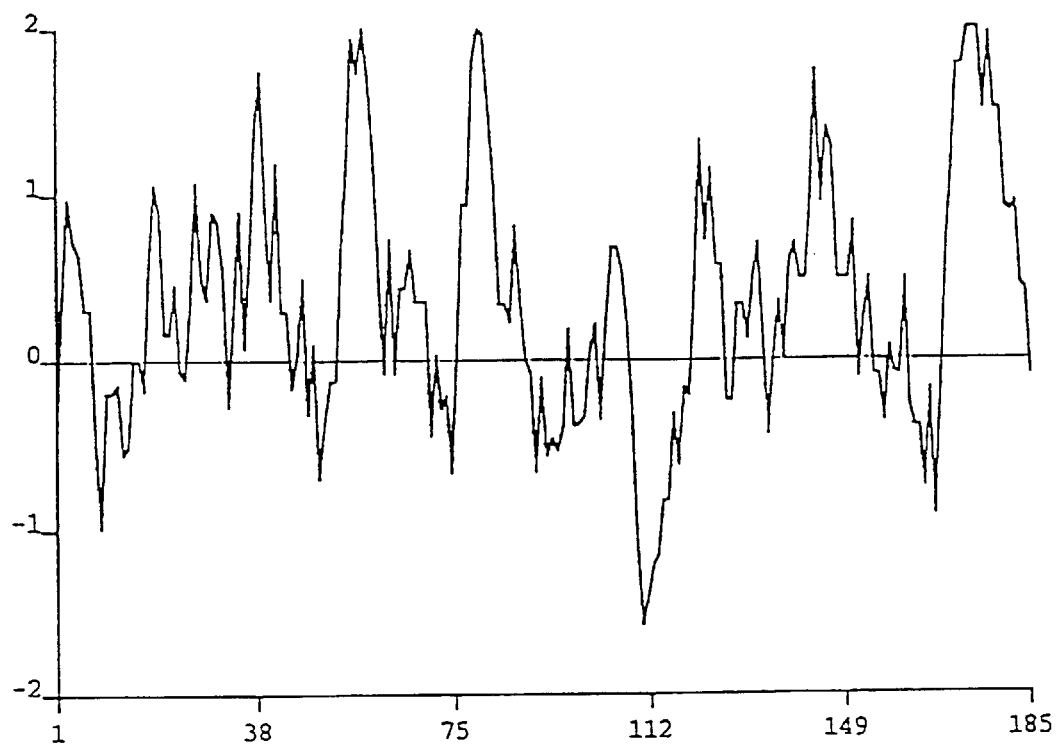
FIG. 3 displays an analysis of the hydrophobicity characteristics of the PAC10 human homolog based on the predicted amino acid sequence.
Figure 4:
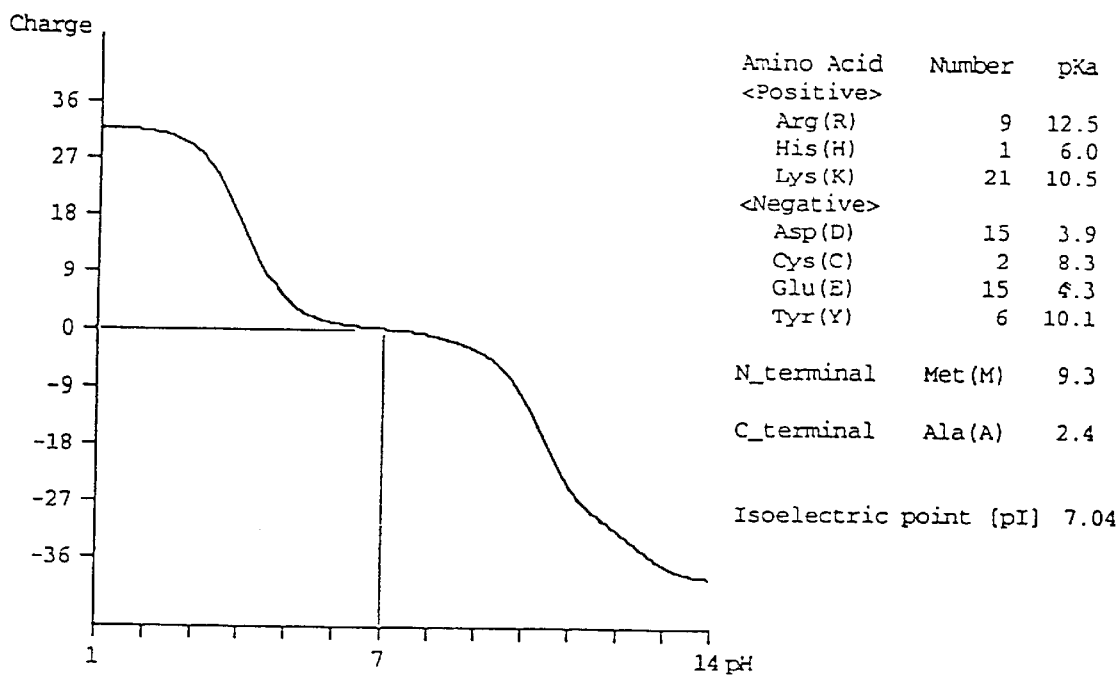
FIG. 4 displays the isoelectric point for the human PAC10 human homolog as determined by MacDNAsis. The results indicate that the isoelectric point [pI] for the PAC 10 human homolog is 7.04.
Figure 5:
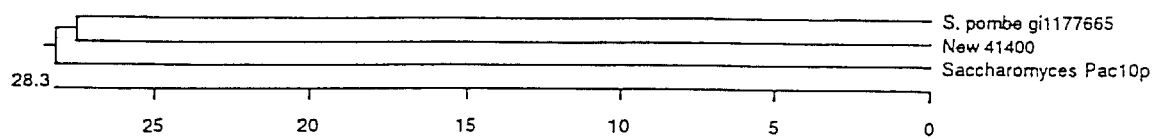
FIG. 5 displays the phylogenic tree for Incyte clone number 41400, S. Pombe and *Saccharomyces cerevisiae* PAC10 protein.

The present invention relates to a novel, human cytoskeletal protein, PAC10 human homolog which has 41% amino acid sequence identity to the pac10 gene of *S. cerevisiae* that encodes heavy chain member of the kinesin family. Nucleic acid sequences encoding the PAC10 human homolog have been mapped to the X chromosome disease locus Xq27-q28 found to be associated with X-linked mental retardation, schizophrenia, and congenital myophathies such as centronuclear myopathy.

The present invention relates to the use of the pac10 human homolog nucleic acid and PAC 10 human homolog amino acid sequences disclosed herein in the diagnosis and treatment of disease states mapped to the Xq27-q28 disease locus.

The present invention also relates to the use of the pac10 human homolog nucleic acid sequences for the detection of mutations, including deletions and translocations in the gene encoding the PAC10 human homolog. Such nucleic acid sequences could be used for the in utero fetal diagnosis of diseases such X-linked mental retardation and X-linked congenital myophathies, such as the neonatal form of centronuclear myopathy.

The present invention also relates to the use of the PAC10 human homolog and genetically engineered host cells that express the PAC10 human homolog to evaluate, screen and identify substances, compounds or synthetic drugs that modulate the activity of the PAC10 human homolog.

"Nucleic acid sequence" as used herein refers to an oligonucleotide, nucleotide or polynucleotide sequence, and fragments or portions thereof, and to DNA or RNA of genomic or synthetic origin which may be double-stranded or single-stranded, whether representing the sense or anti-sense strand. As used herein "amino acid sequence" refers to peptide or protein sequences or portions thereof. As used herein, lower case "pac10 human homolog" refers to a nucleic acid sequence whereas upper case "PAC10 human homolog" refers to a protein sequence. As used herein, peptide nucleic acid (PNA) refers to a class of informational molecules that have a neutral "peptide like" backbone with nucleobases that allow molecules to hybridize to complementary DNA or RNA with higher affinity and specificity than corresponding oligonucleotides (PerSeptive Biosystems 1-800-899-5858).

As used herein, PAC10 encompasses PAC10 from any mammalian species, including bovine, ovine, murine, porcine, equine and preferably human sources, in naturally occurring or in variant form, or from any source, whether natural, synthetic, semi-synthetic or recombinant.

As used herein, "naturally occurring" refers to PAC10 with an amino acid sequence found in nature, and "biologically active" refers to PAC10 having structural, regulatory or biochemical functions of the naturally occurring protein. As used herein, "immunological activity" is defined as the capability of the natural, recombinant or synthetic PAC10 or any oligopeptide thereof, to induce a specific immune response in appropriate animals or cells and to bind with specific antibodies.

The term "derivative" as used herein refers to the chemical modification of PAC10 human homolog. Illustrative of such modifications is replacement of hydrogen by an alkyl, acyl, or amino group. A PAC10 protein derivative retains essential biological characteristics of the naturally occurring protein.

As used herein, the term "purified" refers to molecules, either nucleic or amino acid sequences, that are removed from their natural environment and isolated or separated from at least one other component with which they are naturally associated.

The Coding Sequences

The nucleotide sequence of the pac10 human homolog (SEQ ID NO:1) is shown in FIG. 1. The nucleotide sequence of the pac10 human homolog was initially found among the nucleotide sequences of a cDNA library made from hybrid cells of T-B lymphoblasts from a leukemic cell line where it was found two times in 3071 usable nucleotide sequences.

Nucleotide sequence encoding a portion of the PAC10 human homolog were also found one time in 640 usable sequences of a cDNA library made from kidney tissue (Incyte library KIDNNOT01); one time in 1404 usable sequences of a cDNA library made from colon tissue (Incyte library COLNNOT09); three times in 5262 usable sequences of a cDNA library made from the hNT teratocarcinoma cell line (Incyte library HNT2AGT01); one time in 2018 usable sequences of a cDNA library made from the U937 monocyte cell line (Incyte library U937NOT01); one time in 2214 usable sequences of a cDNA library made from the THP-1 promonocyte cell line treated with PMA and LPS (Incyte library THP1PLB01); one time in 2460 usable sequences of a cDNA library made from the TBP-1 promonocyte cell line treated with PMA and LPS (Incyte library THP1PLB02); one time in 2952 usable sequences of a cDNA library made from tonsil tissue of an individual having lymphoid hyperplasia (ancyte library TONSNOT01); one time in 3013 usable sequences of a cDNA library made from prostate tissue (Incyte library PROSNOT06); one time in 2319 usable sequences of a cDNA library made from bone marrow (Incyte library BMARNOT02); one time in 3742 usable sequences of a cDNA library made from lung tissue (Incyte library LUNGNOMO1); one time in 5810 usable sequences of a cDNA library made from the bNT2 teratocarcinoma cell line (Incyte library HNT2NOT01); one time in 7953 usable sequences of a cDNA library made from melanocytes (Incyte library MELANOM01); and two times in 22,260 usable sequences of a cDNA library made from infant brain (BRAINOM01). As used herein, the term usuable sequence refers to the total number of clones in a library after the removal of vector, nucleotide repeats, contamination, and mitochrondrial DNA.

The full length cDNA of the pac10 human homolog was searched against public protein databases using the BLAST algorithm which stands for Basic Local Alignment Search Tool (Altschul S F (1993) J Mol Evol 36:290–300; Altschul, S F et al (1990) J Mol Biol 215:403–10) and was found to have about 50% nucleic acid sequence homology to the Saccharomyces cerevisiae pac10 gene which encodes heavy chain members of the kinesin. A BLAST search against GenpeptV92 revealed that the PAC10 amino acid sequence has a more distant relationship to the beta cardiac myosin heavy chain (Oryctolagus cuniculus) and the neuronal myosin heavy chain (Rattus rattus). The PAC10 amino acid sequence also has homology to the serotonin receptors NCBI Entrez accession numbers GI 177776 and GI 36431.

The nucleotide sequence of SEQ ID NO:1 encodes a PAC10 human homolog (SEQ ID NO:2) having 201 amino acids, having a predicted molecular weight of 21447.45 Daltons and an isoelectric point [pi] of 7.04.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thernostable T7 polymerase (Amersham, Chicago Ill.), or combinations of recombinant polymerases and proofreading exonucleases such as the ELONGASE Amplification System marketed by Gibco BRL (Gaithersburg Md.). Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.), the ABI Catalyst 800, and ABI 377 and 373 DNA sequencers (Perkin Elmer, Norwalk Conn.).

The quality of any particular cDNA library in which polynucleotides encoding the PAC10 human homolog are found may be determined by performing a pilot scale analysis of the cDNAs and checking for percentages of clones containing vector, lambda or E. coli DNA, mitochondrial or repetitive DNA, and clones with exact or homologous matches to public databases.

Extending Polynucleotide Sequences

The polynucleotide sequence encoding the PAC10 human homolog may be extended utilizing the nucleotide sequences from SEQ ID NO:1 in various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al(1988) Nucleic Acids Res 16:8186). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method which permits retrieval of unknown sequence. PromoterFinder™ is a new kit available from Clontech (Palo Alto Calif.) which uses PCR, nested primers and special libraries to "walk in" genomic DNA. This process avoids the need to screen libraries and is useful in finding intron/exon junctions.

Another PCR method, "*Improved Method for Obtaining Full Leng cDNA Sequences*" by Guegler et al, pending patent application Ser. No. 08/487,112, filed Jun. 7, 1995 and hereby incorporated by reference, employs XL-PCR™ enzymes (Perkin-Elmer, Foster City Calif.) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are usefull for obtaining introns and extending 5' sequence.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies.

Capillary sequencing employs flowable polymers for electrophoretic separation, four different fluorescent dyes (one for each nucleotide) which are laser activated, and detection of the emitted wavelengths by a charge coupled devise camera Output/light intensity is converted to electrical signal using appropriate software (eg. Genotyper™ and Sequence Navigator™ programs from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression Systems

In accordance with the present invention, pac10 human homolog polynucleotide sequences which encode the PAC10 human homolog, fragments of the polypeptide, fusion proteins or functional equivalents thereof, may be used to generate recombinant DNA molecules that direct the expression of the pac10 human homolog in appropriate host cells. Due to the inherent degeneracy of the genetic code, other DNA sequences which encode substantially the same or a functionally equivalent amino acid sequence, may be used to clone and express the PAC10 human homolog. As will be understood by those of skill in the art, it may be advantageous to produce PAC10 encoding human homolog nucleotide sequences possessing non-naturally occurring codons. Codons preferred by a particular prokaryotic or eukaryotic host (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of SEQ ID NO:1 under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences. The term "hybridization" as used herein shall include "the process by which a strand of nucleic acid joins with a complementary strand through base pairing" (Coombs J (1994) *Dictionary of Biotechnology*, Stockton Press, New York N.Y.). The process of amplification often follows the process of hybridization. The process of amplification as carried out in polymerase chain reaction technologies is described in Dieffenbach C W and G S Dveksler (1995, *PCR Primer, a Lab Manual*, Cold Spring Harbor Press, Plainview N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring pac10 human homolog.

As used herein "substitution" results from the replacement of one or more nucleotides or amino acids by different nucleotides or amino acids, respectively.

Altered pac10 human homolog polynucleotide sequences which may be used in accordance with the invention include deletions, insertions or substitutions of different nucleotide residues resulting in a polynucleotide that encodes the same or a functionally equivalent PAC10 human homolog. The protein may also show deletions, insertions or substitutions of amino acid residues which produce a silent change and result in a functionally equivalent PAC10 human homolog. Deliberate amino acid substitutions may be made on the basis of similarity in polarity, charge, solubility, hydrophobicity, hydrophilicity, and/or the amphipathic nature of the residues as long as the biological activity of the PAC10 human homolog is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

Included within the scope of the present invention are alleles of the pac10 human homolog. As used herein, an "allele" or "allelic sequence" is an alternative form of the pac10 human homolog. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a pac10 human homolog coding sequence for a variety of reasons, including but not limited to, alterations which modify the cloning, processing and/or expression of the gene product. For example, mutations may be introduced using techniques which are well known in the art, eg, ite-directed mutagenesis to insert new restriction sites, to alter glycosylation patterns or to change codon preference, for example.

In another embodiment of the invention, a pac10 human homolog natural, modified or recombinant sequence may be ligated to a heterologous sequence to encode a fusion protein. For ample, for screening of peptide libraries for modulators of pac10 human homolog activity, it may be useful to encode a chimeric PAC10 human homolog protein expressing a heterologous epitope that is recognized by a commercially available antibody. A fusion protein may also be engineered to contain a cleavage site located between the pac10 nucleotide sequence and the heterologous protein sequence, so that the PAC10 human homolog protein may be cleaved and purified away from the heterologous moiety.

In an alternate embodiment of the invention, the coding sequence of pac10 human homolog could be synthesized, in whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a PAC10 human homolog amino acid sequence, in whole or in part. For example, peptides can be synthesized by solid phase techniques, cleaved from the resin, and purified by preparative high performance liquid chromatography (eg, Creighton (1983) *Proteins Structures And Molecular Principles*, W H Freeman and Co, New York N.Y.). The composition of the synthetic peptides may be confirmed by amino acid analysis or sequencing (eg, the Edman degradation procedure; Creighton, supra)

Direct peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer. Additionally, the amino acid sequence of the PAC10 human homolog, or any part thereof, may be altered during direct synthesis and/or combined using chemical methods with sequence from other a subunits, or any part thereof, to produce a variant polypeptide.

Identification of Transformants

Although the presence/absence of marker gene expression suggests that the gene of interest is also present, its presence and expression should be confirmed. For example, if the pac10 human homolog is inserted within a marker gene sequence, recombinant cells containing the PAC10 human homolog insert can be identified by the absence of marker gene function.

Alternatively, a marker gene can be placed in tandem with a pac10 human homolog sequence under the control of a single promoter. Expression of the marker gene in response to induction or selection usually indicates expression of the PAC10 human homolog as well.

Alternatively, host cells which contain the coding sequence for PAC10 human homolog and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the pac10 human homolog polynucleotide sequence can be detected by DNA-DNA or DNA-RNA hybridization or amplification using probes, portions or fragments disclosed in SEQ ID NO:1. Nucleic acid amplification based assays involve the use of oligonucleotides or oligomers based on SEQ ID NO:1 to detect transformants containing the pac10 human homolog nucleic acid. As used herein "oligonucleotides" or "ligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the pac10 human homolog nucleotide sequence shown in FIG. 1.

A variety of protocols for detecting and measuring the expression of a PAC10 homolog polypeptides, using either polyclonal or monoclonal antibodies specific for the protein are known in the art. Examples include enzyme4inked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on a PAC10 homolog polypeptide is preferred, but a competitive binding assay may be employed. These and other assays are described, among other places, in Hampton R et al (1990, *Serological Methods, a Laboratory Manual*, APS Press, St Paul Minn.) and Maddox Del. et al (1983, J Exp Med 158:1211).

A wide variety of labels and conjugation techniques are known by those skilled in the art and can be used in various nucleic and amino acid assays. Means for producing labeled hybridization or PCR probes for detecting pac10 human homolog polynucleotide sequences include oligolabeling, nick translation, end-labeling or PCR amplification using a labeled nucleotide. Alternatively, the pac10 nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 and incorporated herein by reference.

Purification of PAC10 Human Homolog

Host cells transformed with pac10 human homolog nucleotide sequences may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing a pac10 human homolog can be designed with signal sequences which directs secretion of the PAC10 human homolog through a particular prokaryotic or eukaryotic cell membrane. Other recombinant constructions may join the pac10 human homolog polynucleotide sequences to nucleotide sequence encoding a polypeptide domain which will facilitate purification of soluble proteins (Kroll D J et al (1993) DNA Cell Biol 12:441–53; see also above discussion of vectors containing fusion proteins).

The PAC10 human homolog may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif3:263–1), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the PAC10 human homolog is useful to facilitate purification.

Uses of PAC10 and Genetically Engineered Host Cells Containing PAC10.

The amino acid sequence of the PAC 10 human homolog is shown in FIG. 1. Based upon its homology to S.cerevisiae PAC10 and the localization of nucleic acid encoding PAC10 to the disease locus Xq27-q28, the human PAC10 homolog disclosed herein appears to be a cytoskeletal protein that is associated with the disease locus Xq27-q28.

Accordingly, the present invention provides PAC10 human homolog amino acid sequences and genetically engineered host cells that express the sequences to evaluate, screen and identify substances compounds or synthetic drugs that modulate the activity of the PAC10 human homolog.

In an embodiment of the present invention, PAC10 human homolog or a variant thereof and/or a cell line that expresses the PAC10 human homolog or variant thereof may be used to screen for antibodies, peptides, or other molecules, such as organic or inorganic molecules made by combinatorial chemistry, that act as modulators of the PAC10 human homolog activity. Anti-PAC10 antibodies capable of neutralizing the activity of the PAC10 human homolog may be identified. Synthetic compounds, natural products, and other sources of potentially biologically active materials can be screened in a number of ways deemed to be routine to those of skill in the art.

Antibodies

Procedures well known in the art may be used for the production of antibodies to PAC10 human homolog polypeptides. Such antibodies include, but are not limited to, polyclonal, monoclonal, chimeric, single chain, Fab fragments and fragments produced by a Fab expression library. Neutralizing antibodies, ie, those which inhibit biological activity of PAC10 human homolog polypeptides, are especially preferred for diagnostics and therapeutics. Anti-PAC10 human homolog antibodies can be used to localize or detect PAC10 human homolog in dividing cells thereby providing a qualitative measurement of PAC10 function.

For the production of antibodies, various hosts including goats, rabbits, rats, mice, etc may be immunized by injection with PAC10 human homolog polypeptide or any portion, fragment or oligopeptide which retains immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calnette-Guerin) and *Corynebacterium parvum* are potentially useful human adjuvants which may be employed if purified PAC10 human homolog polypeptide is administered to individuals. Monoclonal antibodies to PAC10 human homolog polypeptide may be prepared using any technique which provides for the production of antibody molecules by continuous cell lines in culture. These include, but are not limited to, the hybridoma technique originally described by Koehler and Milstein (1975, Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C. (1991; Nature 349:293–299).

Antibody fragments which contain specific binding sites for the PAC10 human homolog may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275–1281).

PAC10 human homolog-specific antibodies are useful for the diagnosis of conditions and diseases associated with expression of PAC 10 human homolog polypeptide. A variety of protocols for competitive binding or immunoradiometric assays using either polyclonal or monoclonal antibodies with established specificities are well known in the art. Such immunoassays typically involve the formation of a complex between a protein and its specific antibody and the measurement of complex formation. A two-site, monoclonal-based immunoassay utilizing monoclonal antibodies specific for two noninterfering epitopes on a specific PAC10 human homolog protein is preferred, but a competitive binding assay may also be employed. These assays are described in Maddox DE et al (1983, J Exp Med 158:1211).

Diagnostic Assays Using PAC10 Specific Antibodies

Anti-PAC10 human homolog antibodies are useful for the diagnosis of diseases and conditions associated with PAC10 human homolog activity, such as, centronuclear myopathy, myotubular myopathy, schizophrenia, X-linked mental retardation associated with Fragile Site FRAXE and anophthalmos. Diagnostic assays for the detection of the PAC10 human homolog include methods utilizing the antibody and a label to detect the PAC10 human homolog polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known to those of skill in the art.

A variety of protocols for measuring a PAC10 human homolog polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on a PAC10 human homolog polypeptide is preferred, but a competitive binding assay may be employed. These assays are described, among other places, in Maddox, D E et al (1983, J Exp Med 158:1211).

In order to provide a basis for the diagnosis of disease, normal or standard values for the PAC10 human homolog polypeptide expression are established. This is accomplished by combining body fluids or cell extracts taken from normal subjects, either animal or human, with antibody to a PAC10 human homolog polypeptide under conditions suitable for complex formation using techniques which are well known in the art. The amount of standard complex formation can be quantified by comparing it with a dilution series of positive controls where a known amount of antibody is combined with known concentrations of purified PAC10 human homolog polypeptide. Then, standard values obtained from normal samples may be compared with values obtained from samples from subjects potentially affected by a disorder or disease elated to PAC10 human homolog expression. Deviation between standard and subject values establishes the presence of the disease state.

Drug Screening

A PAC10 human homolog polypeptide, its immunogenic fragments or oligopeptides thereof can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between a PAC10 human homolog polypeptide and the agent being tested, may be measured. Accordingly, the present invention provides a method for screening a plurality of compounds for specific binding affinity with PAC10 human homolog or a fragment thereof, comprising providing a plurality of compounds; combining a PAC10 human homolog of the present invention or a fragment thereof with each of a plurality of compounds for a time sufficient to allow binding under suitable conditions; and detecting binding of the PAC10 human homolog, or fragment thereof, to each of the plurality of compounds, thereby identifying the compounds which specifically bind the PAC10 human homolog. In such an assay, the plurality of compounds may be produced by combinatorial chemistry techniques known to those of skill in the art.

Another technique for drug screening provides for high throughput screening of compounds having suitable binding affinity to a PAC10 human homolog polypeptide and is described in detail in Geysen, European Patent Application 84/03564, published on Sep. 13, 1984. In summary, large numbers of different small peptide test compounds are synthesized on a solid substrate, such as plastic pins or some other surface. The peptide test compounds are reacted with PAC10 human homolog fragments and washed. A bound PAC10 human homolog of the present invention is then detected by methods well known in the art. A purified PAC10 human homolog can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding the PAC10 human homolog specifically compete with a test compound for binding the PAC10 human homolog. In this manner, the antibodies can be used to detect the presence of any peptide which shares one or more antigenic determinants with the PAC10 human homolog.

Uses of the Pac10 Human Homolog Polynucleotide Sequences

A pac10 human homolog polynucleotide, or any part thereof, provides the basis for diagnostic and/or therapeutic compounds. For diagnostic purposes, PAC10 human homolog polynucleotide sequences are used to detect and quantitate gene expression in conditions, disorders and diseases in which their activity may be implicated, for example, in centronuclear myopathy, myotubular myopathy, schizophrenia, X-linked mental retardation associated with Fragile Site FRAXE and anophthalmos. For therapeutic purposes, pac10 homolog antisense molecules are administered to individuals in conditions where it is desirable to regulate the Pac10 homolog gene thereby inhibiting its activity. Alternatively, for therapeutic purposes, sense polynucleotide sequences encoding PAC10 human homolog or sequences thereof are administered to individuals in conditions where it is desirable to replace a naturally occurring mutated polynucleotide sequence, i.e. a pac10 human homolog polynucleotide sequence that has been subject to a translocation, deletion, or point mutation, or to augment a naturally occurring polynucleotide sequence.

Included in the scope of the invention are oligonucleotide sequences, antisense RNA and DNA molecules and ribozymes, which function to destabilize pac10 human homolog mRNA or inhibit translation of a pac 10 human homolog.

Another aspect of the subject invention is to provide for nucleic acid hybridization or PCR probes which can detect polynucleotide sequences, including genomic sequences, encoding PAC10 human homolog, or closely related molecules, such as alleles. In one embodiment of the present invention, pac10 human homolog polynucleotide sequences are used as probes in diagnostic assays for the detection of mutations, deletions and mutations in the naturally occurring polynucleotide sequences.

Diagnostic Uses of Pac10 Polynucleotide

A PAC10 human homolog encoding polynucleotide sequence may be used for the diagnosis of diseases associated with the disease locus Xq27-q28. For example, polynucleotide sequences encoding PAC10 human homolog can be used in hybridization or PCR assays of tissues from biopsies or autopsies or biological fluids, such as serum, amniotic fluid, or muscle biopsy. Such qualitative or quantitative methods include Southern or northern analysis, dot blot or other membrane-based technologies; PCR technologies; dip stick, pin or chip technologies; and ELISA or other multiple sample format technologies. All of these techniques are well known in the art and are in fact the basis of many commercially available diagnostic kits. Specific pac10 human homolog polynucleotide probes can be designed for use in hybridization based diagnostic assays to ascertain if a naturally occurring pac10 human homolog polynucleotide sequence contains a nucleic acid mutation or deletion or has been subject to a translocation. In particular, such assays could be used to detect the presence of X-linked congenital abnormalites, such as neonatal centronuclear myopathy, in fetal nucleic acid derived from amniotic or chorionic villus samples. Early detection of congenital defects, such as centronuclear myopathy, alerts physicians and health care professionals and provides the opportunity for genetic counseling and/or early therapeutic intervention.

Hybridization assays can be tailored to evaluate the efficacy of a particular therapeutic treatment regime and are used in animal studies, in clinical trials, or in monitoring the treatment of an individual patient. For disease diagnosis, a normal or standard profile for expression is first established.

This is accomplished by combining body fluids or cell extracts taken from normal subjects, either animal or human, with pac10 homolog polynucleotide sequences or a portion hereof, under conditions suitable for hybridization or amplification. Standard hybridization is quantified by comparing the values obtained for normal subjects with a dilution series of positive controls run in the same experiment where a known amount of a purified pac10 polynucleotide sequence is used. Standard values obtained from normal samples are compared with values obtained from samples from subjects potentially affected by a disorder or disease related to pac10 human homolog expression. Deviation between standard and subject values establishes the presence of the disease state. If disease is established, an existing therapeutic agent or therapy plan is administered, and treatment profile or values may be generated. Finally, the assay may be repeated on a regular basis to evaluate progress toward the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the pac10 human homolog polynucleotide sequence. Such oligomers are generally chemically synthesized, but they are generated enzymatically or produced from a recombinant source. Oligomers generally comprise two nucleotide sequences, one with sense orientation (5'-<3') and one with antisense (3'<-5') employed under optimized conditions for identification of a specific gene or condition. The same two oligomers, nested sets of oligomers, or even a degenerate pool of oligomers are employed under less stringent conditions for detection and/or quantitation of closely related DNA or RNA sequences.

Additionally methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples is speeded up by running the assay in an ELISA format where the oligomer of interest is supplied in various dilutions and a spectrophotometric or colorimetric response gives rapid quantitation.

Therapeutic Uses of a Pac10 Human Homolog Polynucleotide

A pac10 human homolog antisense molecule can provide the basis for treatment of various abnormal conditions associated with the disease locus Xq27-q28 where it would be desirable to downregulate the presence of naturally occurring pac10 human homolog or a mutated pac10 human homolog, thereby inhibiting its activity. Alternatively, polynucleotide sequences encoding PAC10 human homolog may provide the basis for gene therapy in the treatment of various abnormal conditions where it is desirable to introduce the pac10 gene or up-regulate the presence of PAC10 human homolog thereby enhancing its activity, for example in conditions where the naturally occurring sequence has been mutated.

Expression vectors derived from retroviruses, adenovirus, herpes or vaccinia viruses, or from various bacterial plasmids, are used for delivery of recombinant pac10 human homolog sense or antisense molecules to the targeted cell population. Methods which are well known to those skilled in the art can be used to construct recombinant vectors containing pac10 human homolog-related nucleotide sequences. See, for example, the techniques described in Maniatis et al (supra) and Ausubel et al(supra).

Alternatively, recombinant pac10 human homolog can be delivered to target cells in liposomes.

The full length cDNA sequence and/or its regulatory elements enable researchers to use pac10 human homolog nucleic acid as a tool in sense (Youssoufian H and HF Lodish 1993 Mol Cell Biol 13:98–104) and antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions.

Additionally, pac10 human homolog expression can be modulated by transfecting a cell or tissue with expression vectors which express high levels of a pac10 human homolog fragment in conditions where it would be preferable to inhibit its activity. Such constructs can flood cells with untranslatable sense or antisense sequences which compete for binding with the naturally occurring PAC10 human homolog. Even in the absence of integration into the DNA, such vectors may continue to transcribe RNA molecules until all copies of the vector are disabled by endogenous nucleases. Such transient expression may last for a month or more with a non-replicating vector (Mettler I, personal communication) and even longer if appropriate replication elements are part of the vector system.

Stable transformation of appropriate germ line cells, or preferably a zygote, with a vector containing pac10 human homolog sense or antisense nucleic acid, or fragments thereof, may produce a transgenic organism that produces enough copies of the sense or antisense sequence to significantly modify the activity of the endogenous pac10 human homolog nucleic acid. A pac10 human homolog sense nucleic acid fragment can be introduced into an organism when it is desirable to augment the presence of the endogenous pac10 human homolog or to overcome the presence of an endogenous form of the pac10 human homolog that is aberrant, ie subject to a mutation, deletion or translocation. A pac10 antisense nucleic acid fragment can be introduced into an organism when it is desirable to eliminate the activity of the endogenous pac10 nucleic acid.

Modifications of gene expression can be obtained by designing antisense sequences to the control regions of the pac10 human homolog gene, such as the promoters, enhancers, and introns. Oligonucleotides derived from the transcription initiation site, eg, between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of pac10 human homolog RNA sequences.

Specific ribozyme cleavage sites within any potential RNA target are initially identified by scanning the target molecule for ribozyme cleavage sites which include the following sequences, GUA, GOU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Methods for introducing vectors into cells or tissue include those methods discussed infra. In addition, several of these transformation or transfection methods are equally suitable for a vivo therapy, Furthermore, the pac10 human homolog polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Pac10 Human Homolog Polynucleotide Sequences

The nucleic acid sequence for the pac10 human homolog can also be used to generate hybridization probes as previously described, for mapping the endogenous genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1995; 270:410f and 1994; 265:19811). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as myotubular myopathy localized by genetic linkage to a particular genomic region, for example, to Xq27-q28 (Dahl et al. 1995 Am. J. Hum. Genet. 56:1108–1115), any additional sequences mapping to that area may represent associated or regulatory genes for further investigation. The nucleotide sequence of the subject invention may also be used to detect differences in the chromosomal location due to translocation, inversion, etc between normal, carrier or affected individuals.

Pharmaceutical Compositions

The present invention relates to pharmaceutical compositions which may comprise nucleotides, proteins, antibodies, antagonists, or inhibitors, or agonists of PAC10 human homolog in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of pharmaceutical compositions, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors or agonists which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions or locations, for example.

It is contemplated that antagonists or agonists of PAC10 human homolog can be delivered in a suitable formulation to individuals having conditions where it is desirable to inhibit or enhance, respectively, PAC10 human homolog activity.

These examples are provided by way of illustration and are not included for the purpose of limiting the invention.

EXAMPLES

I Construction of the TBLYNOT01 Library

The TBLYNOPT01 library was constructed from the 174×CEM.TI hybrid T+B lymphoblast cell line. The 174× CEM.TL cell line is a cloned somatic cell hybrid of a human T lymphoblastoid cell line, CEM$^R$.3, and a human B lymphoblastoid cell line, 721.174, which was produced by PEG-mediation fusion as described in Salter et al. (1985) *Immunogenetics* 21:235–246. The hybrid cell line expresses class II antigens encoded by CEMR.3, HLA class I antigens encoded by both parental cell lines, and HLA-B5 and HLA-Bw6 antigens encoded by parental cell lines 721.174 and CEM$^R$.3, respectively. Studies of this cell line indicated that two complementary trans-acting factors mediate enhanced expression of HLA class I antigens in the hybrid, one encoded by a gene on chromosome 6 of CEM$^R$.3, and the other encoded by the genome of 721.174 previously postulated to induce expression of CEM$^R$.3-encoded class I antigens in hybrids of CEM$^R$.3 with B lymphoblastoid cell lines (Salter et al. (1985)).

Poly(A+) RNA (mRNA) was purified from the 174×CEM.TL cell line. The RNA was primed with oligo dT and cDNA was synthesized from the mRNA. Synthetic adaptor oligonucleotides were ligated onto cDNA ends enabling its insertion into Uni-ZAP™ DR vector system (Stratagene), allowing high efficiency unidirectional (sense orientation) lambda library construction and the convenience of a plasmid system with blue/white color selection to detect clones with cDNA insertions. Alternative unidirectional vectors include but are not limited to pcDNAI (Invitrogen) and pSflox-1 (Novagen).

The 174×CEM.TL cell line lambda cDNA library (Catalog No. 937214, Stratagene) can be screened with either DNA probes or antibody probes and the pBluescript® phagemid (Stratagene) can be rapidly excised in vivo. The phagemid allows the use of a plasmid system for easy insert characterization, sequencing, site-directed mutagenesis, the creation of unidirectional deletions and expression of fusion proteins. The library phage particles were infected into E. coli host strain XLI-Blue® (Stratagene), which has a high transformation efficiency, increasing the probability of obtaining rare, under-represented clones in the cDNA library.

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria are selected on medium containing ampicillin. Phagemid DNA was purified using the QIAwell-8 Plasmid Purification System from QIAGEN™, QIAwell PLUS, or QIAwell ULTRA DNA Purification System (QIAGEN Inc., 9259 Eton Ave., Chatsworth, Calif. 91311). This product line provides a convenient, rapid and reliable high-throughput method to lyse bacterial cells and isolate highly purified phagemid DNA using QIAGEN anion-exchange resin particles with EMPORE™ membrane technology from 3M in a multiwell format. The DNA was eluted from the purification resin already prepared for DNA sequencing and other analytical manipulations.

The cDNA inserts from random isolates of the 174×CEM.TL cell line library was sequenced in part by the method of Sanger F and A R Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer), and the reading frame was determined.

II Homology Searching of cDNA Clones and Their Deduced Proteins

Each eDNA was compared to sequences in GenBank using a BLAST search (Basic Local Alignment Search Tool; Altschul S F (1993) J. Mol. Evol. 36: 290–300; Altschul S F et al (1990) J. Mol. Biol. 215:403–410). This method identified Incyte Clone 41400 as a non-exact match to the pac10 gene of S. cerevisiae (GenBank U29137) as well as a match to the serotonin receptors having NCBI Entrez accession numbers GI 177776 and GI 36431.

BLAST was used to search for local sequence alignments. BLAST produces alignments of both nucleotide and amino acid sequences to determine sequence similarity. Because of the local nature of the alignments, BLAST is especially useful in determining exact matches and in identifing homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output II Determination of Reading Frame of cDNA Clone The reading frame of individual cDNA clones obtained from the TBLYNOT01 library was obtained by analyzing the polynucleotide sequences for the presence of start (ATG, GTG, etc.) and stop codons (TGA, TAA, TAG). Typically, one frame will continue throughout the major portion of all of a cDNA sequence and the other two pending frames tend to contain numerous stop codons. Algorithms for determining reading frame have been developed which analyze the occurrence of individual nucleotide bases of each putative codon triplet (e.g., Fickett, J. W. Nucleic Acids Research, 10, 5303 (1982)). Coding DNA tends to contain predominantly certain nucleotides within certain triplet periodicities, such as a significant preference for pyrimidines in the third codon position. These algorithms have been incorporated into widely available software and are used to determine coding potential (and frame) of a given stretch of DNA. This algorithm-derived information, combined with start/stop codon information, was used to determine proper frame of individual clones within the library with a high degree of certainty, thus permitting the correct reading frame alignment with appropriate expression vehicles.

IV Extension of PAC10 Human Homolog to Recover Regulatory Elements

The nucleic acid sequence of pac10 human homolog is used to design oligonucleotide primers for obtaining full length sequences from genomic libraries. One primer is synthesized to initiate extension in the antisense direction (XLR) and the other is synthesized to extend sequence in the sense direction (XLF). The primers allow the known pac10 human homolog sequence to be extended "outward" generating amplicons containing new, unknown nucleotide sequence for the control region of interest. The initial primers are designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region. By following the instructions for the XL-PCR kit (Perkin Ehner) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands are selected and cut out of the gel. Further purification involves using a commercial gel extraction method such as QIAQuick™ (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1/µl T4 polynucleotide kinase are added, and the mixture is incubated at room temperature for 2–3 hours or overnight at 16° C. Competent E coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 are employed to screen cDNAs, mRNAs or genomic DNAs. Although the labeling of oligonucleotides, consisting of about 20 base-pairs, is specifically described, essentially the same procedure is used with larger cDNA fragments. Oligonucleotides are labeled by combining 50 pmol of each oligomer and 250 mCi of $[\gamma^{-32}P]$ adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT ARTM film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The pac10 human homolog sequence, or any part thereof, is used to inhibit in vivo or in vitro expression of endogenous pac10 human homolog, respectively. Although use of antisense oligonucleotides, consisting of about 20 base-pairs, is specifically described, essentially the same procedure is used with larger cDNA fragments. An oligonucleotide based on the coding sequence of the pac10 human homolog is used to inhibit expression of endogenous pac10 human homolog. Using Oligo 4.0, the complementary oligonucleotide is designed from the conserved 5' sequence and used to inhibit either transcription, by preventing promoter binding to the upstream nontranslated sequence, or translation of a pad 0 human homolog transcript by preventing the ribosome from binding to the mRNA.

VII Production of Antibodies

For production of polyclonal antibodies, the deduced amino acid sequence of PAC10 human homolog is analyzed using DNASTAR software (DNASTAR Inc) to determine regions of high immunogenicity and a corresponding oligopeptide is synthesized and used to raise antibodies in rabbits. Analysis to select appropriate epitopes, such as those near the C-terminus or in adjacent hydrophilic regions, is described by Ausubel FM et al (supra). An oligopeptide of about 15 residues in length is synthesized using an ABI Peptide Synthesizer Model 431A (Perkin Elmer, Norwalk, Conn.) using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

VII Purification of PAC10 Human Homolog Using Specific Antibodies

Endogenous or recombinant PAC10 human homolog can be purified by immunoaffinity chromatography using antibodies specific for PAC10 human homolog. An immunoaffinity column is constructed by covalently coupling PAC10 human homolog specific antibody to an activated chromatographic resin such as CnBr-activated Sepharose (Pharmacia Biotech). After the coupling, the resin is blocked and washed according to the manufacturer's instructions.

Media containing PAC10 human homolog is passed over the immunoaffinity column, and the column is washed under conditions that allow the preferential absorbance of PAC10 human homolog (eg, high ionic strength buffers in the presence of detergent). The column is eluted under conditions that disrupt antibody/protein binding (eg, a buffer of pH 2–3 or a high concentration of a chaotrope such as urea or thiocyanate ion), and PAC10 human homolog is collected.

IX Identification of Molecules Which Interact with PAC10 Human Homolog

PAC10 human homolog, or a biologically active fragment thereof, is labeled with $^{125}$I Bolton-Hunter reagent (Bolton, A E and Hunter, W M (1973) Biochem J 133: 529). Candidate small molecules previously arrayed in the wells of a 96 well plate are incubated with the labeled PAC10 human homolog, washed and any wells with labeled PAC10 human homolog complex are assayed. Data obtained using different concentrations of PAC10 human homolog are used to calculate values for the number, affinity, and association of the protein with the candidate molecules.

X. Mapping of the Pac10 Human Homolog to the Xq27-q28 Locus

The pac10 human homolog nucleotide sequence was mapped to the X chromosome and localized to the Xq27-q28 locus by FISH in situ hybridization methods.

Materials and Methods for the FISH in situ Method

Slide preparation

Lymphocytes isolated from human blood were cultured in minimal essential medium (MEM) supplemented with 10% fetal calf serum, and phytohemagglutinin (PHA) at 37 degrees C. for 68–72 hours. The lymphocyte cultures were treated with BrdU (0.1 8mg/ml Sigma) to synchronize the cell population. The synchronized cells were washed three times with serum-free medium to release the block and recultured at 37 degrees C. for 6 hours in MEM with thymidine, 2.5 g/ml (Sigma). Cells were harvested and slides were made by using standard procedures including hypotonic treatment, fixed and air-dried.

In situ Hybrdization and FISH Detection cDNA probes were biotinylated with dATP using the BRL BioNick labeling kit at 15 degrees C. for 2 hr (Heng et al, 1992, Proc. Natl. Acad. Sci. USA 89:9509–9513; Heng et al, 1994, Methods in Molecular Biology: In situ hybridization protocols, K. H. A. Choo, ed, Humana Press, Clifton, N.J., pp. 35–49).

The procedure for FISH detection was performed according to Heng et al., 1992, su and Heng et al 1993, Chromosoma vol. 102:325–332. Slides were baked at 55 degrees C. for 1 hour. After RNase treatment, the slides were denatured in 70% formamide in 2×SSC for 2 minutes at 70 degrees C. followed by dehydration with ethanol. Probes were denatured at 75 degrees C. for 5 minutes in a hybridization mix consisting of 50% formamide and 10% dextran sulphate. Probes were loaded on the denatured slides. After overnight hybridization, slides were washed in 50% formamide in 2×SSC followed by washes in 2×SSC and detected as well as amplified using published methods (Heng et al, 1994, supra). For fluorescence detection, slides are incubated in 3% BSA in 4×SSC prior to incubation with Avidin-FITC. The FISH signals and the DAPI banding pattern was recorded separately by taking photographs, and the assignment of the FISH mapping data with chromosomal bands was achieved by superimposing FISH signals with DAPI banded chromosomes (Heng et al, 1993, supra).

Figure 7:
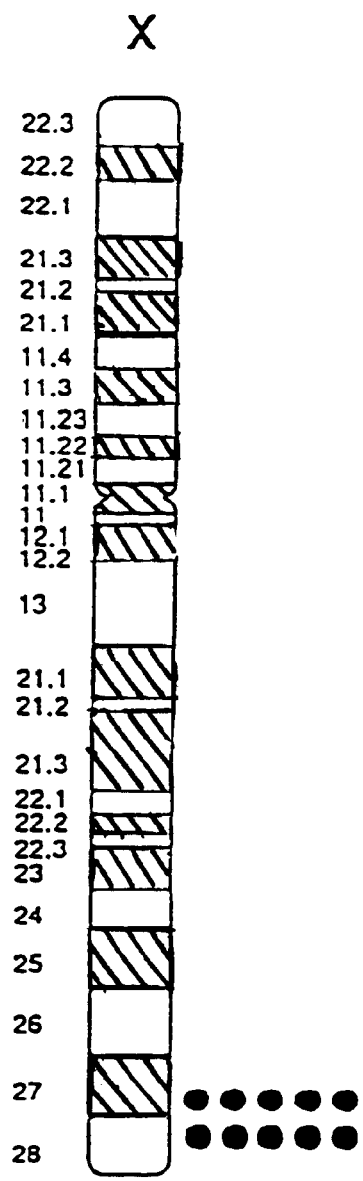
FIG. 7 illustrates that Incyte clone number 41400 is mapped on chromosome Xq27-q28.

Under the conditions used, the hybridization efficiency for clone 41400 was 40%. Clone 41400 was mapped to the X chromosome and localized to the locus Xq27-q28. FIG. 7 illustrates that Incyte clone number 41400 is mapped on chromosome Xq27-q28.

XI. Assembly of Pac10 Nucleotide Sequences

Figure 8A:
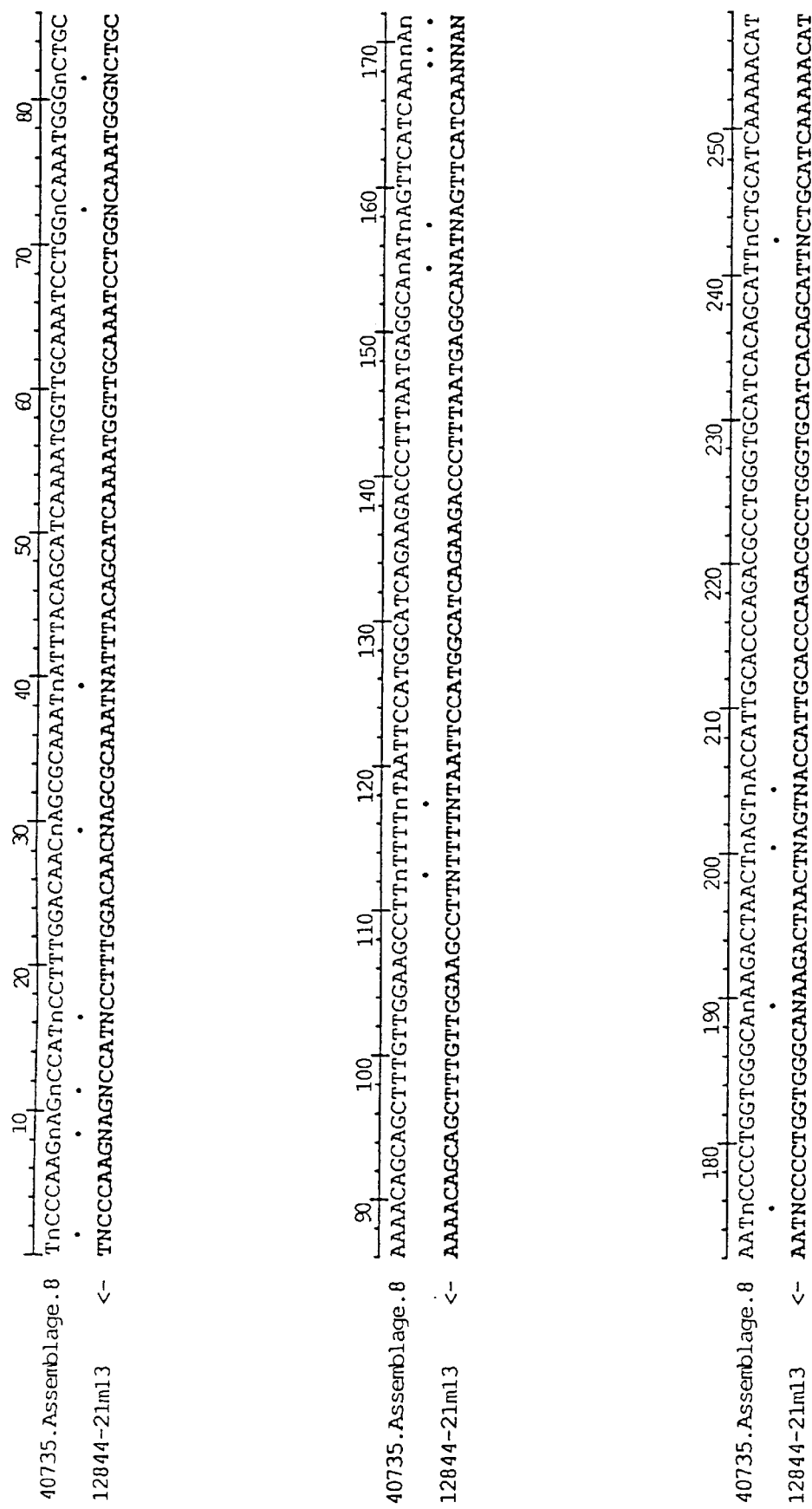
Figure 8C:
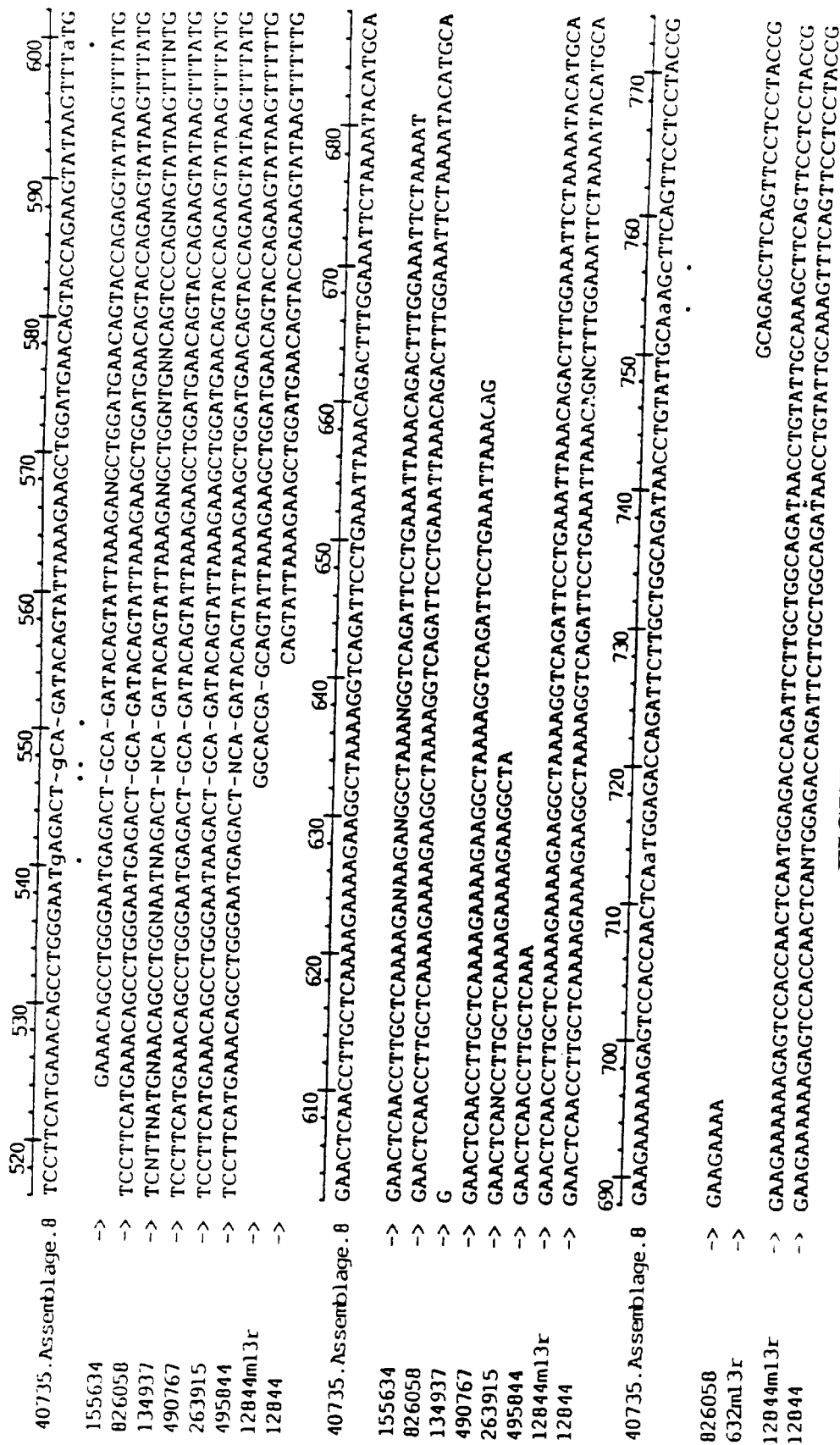
Figure 8D:
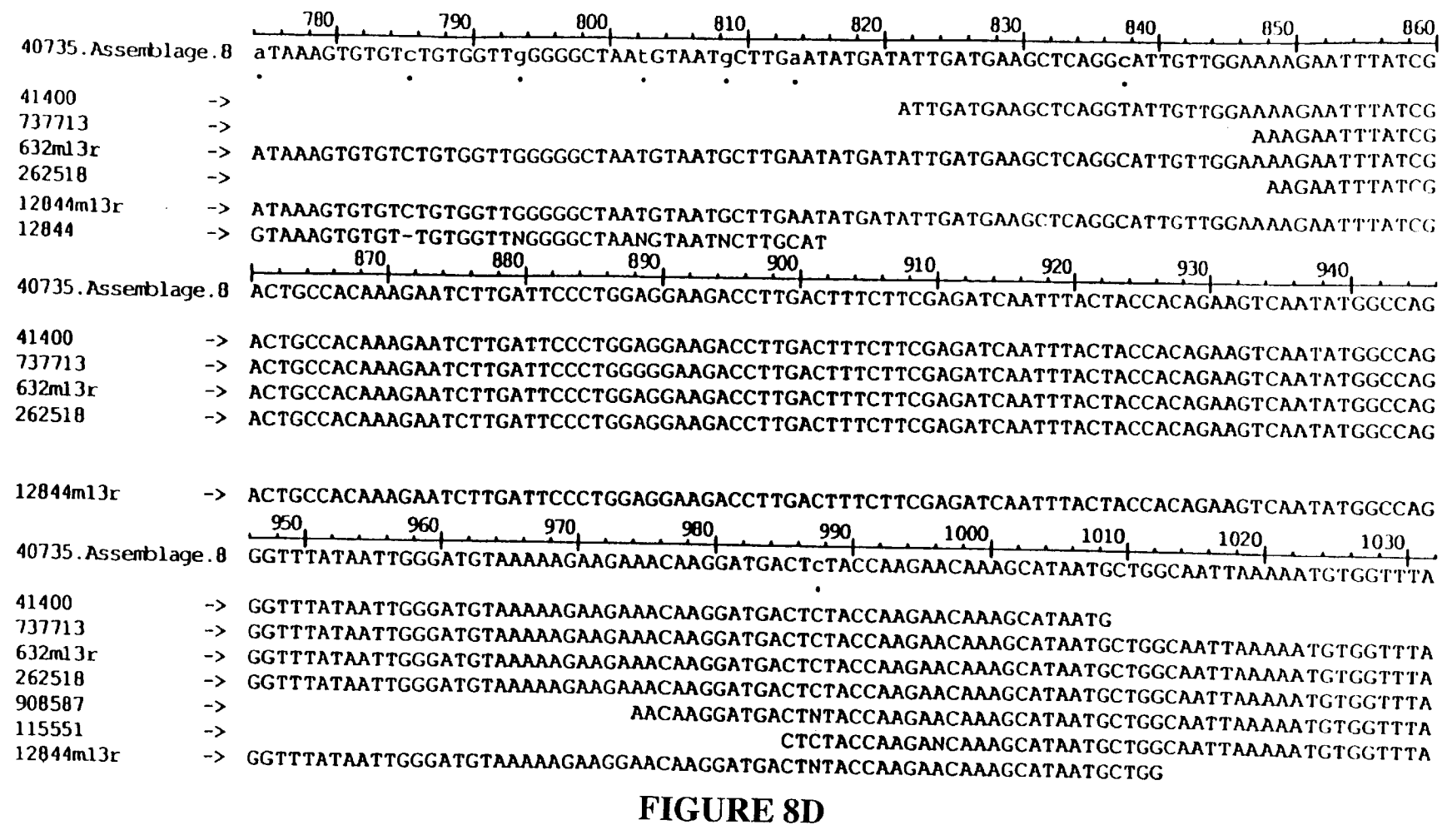
Figure 8E:
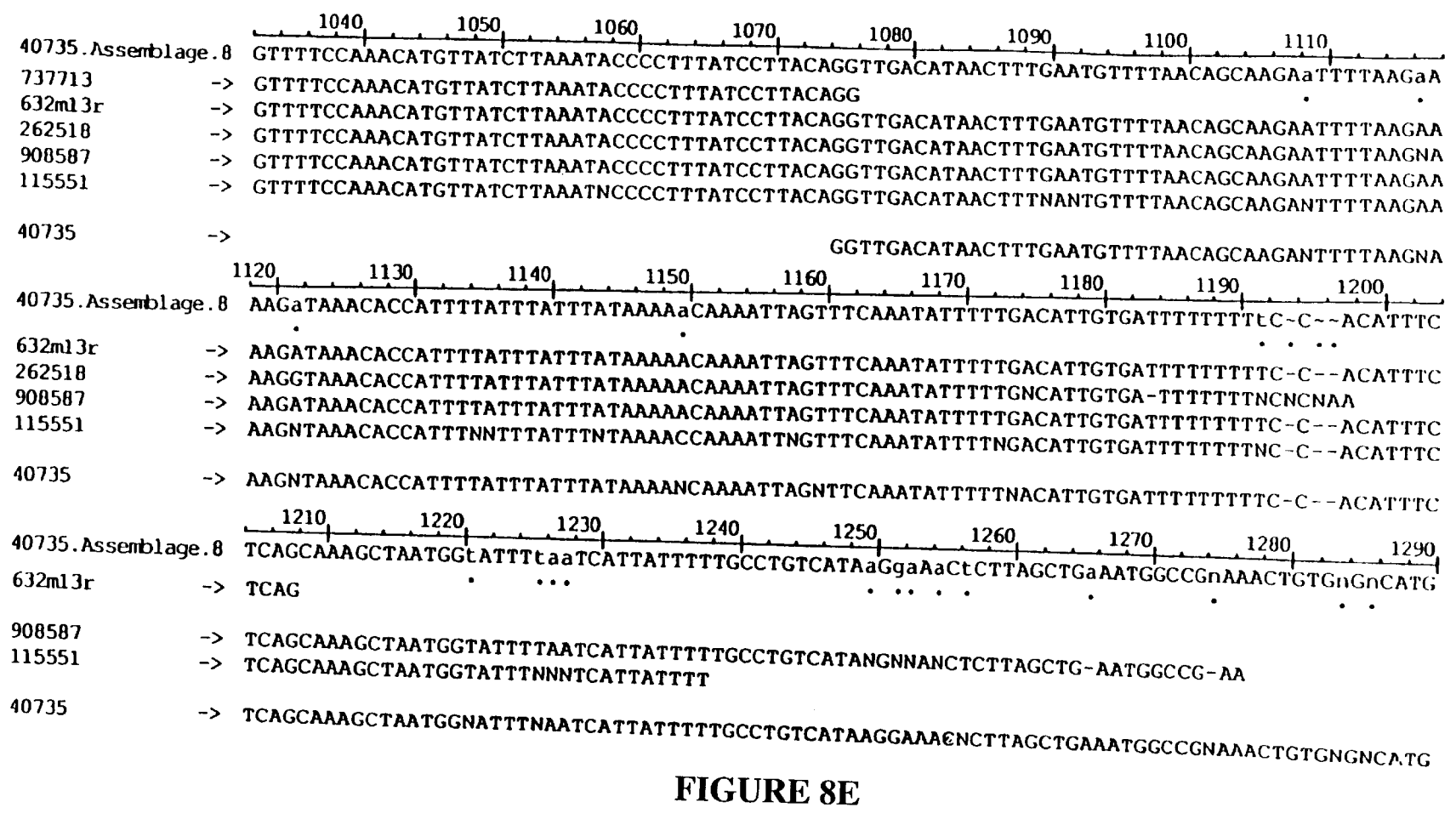

As illustrated in FIG. 8, partial pac10 human homolog cDNA sequences were assembled using the AutoAssembler™ 1.4.0 from Applied Biosystems (ABI). The partial clones used in the assembly were Incyte clones 40735 (Oncyte library TBLYNOT01 made from a leukemic T-B lymphoblast cell line); 12844 (Incyte library THPIPLB01 made from a THP-1 promonocyte cell line treated with PMA and LPS); 826058 (Oncyte library PROSNOT06 made from normal prostate tissue); 134937 (Incyte library BMARNOT02 made from bone marrow); 490767, 263915 and 262518 (Incyte library HNT2AGT01 made from the hNT-2 cell line, post mitotic neurons); 495844 (Incyte library HNT2NOT01 made from the hNT-2 cell line, teratocarcinoma cell line); 155634 (Incyte library THPIPLB02 made from a THP-1 promonocyte cell line treated with PMA and LPS); 000632 (ncyte library U937NOT01 made from the U937 monocyte cell line); 737713 (Incyte library TONSNOT01 made from tonsil tissue from an individual with lymphoid hypeiplasia of the tonsils); 41400 (Incyte library TBLYNOT01 Imade from leukemic T-B lymphoblasts); 908587 (Incyte library COLNNOT09 made from colon tissue); and 115551 (Incyte library KIDNNOT01 made from kidney tissue). Differences in nucleotide sequences, such as those occurring at nucleotide position 599 of Figure 8, may reflect inter-individual genetic variation.

All publications and patents mentioned in the above specification are herein corporated by reference. Various modifications and variations of the described methods and stem of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide comprising a sequence of SEQ ID NO:1.

2. An isolated and purified polynucleotide which is the complement of the polynucleotide of claim 1.

3. An expression vector comprising the polynucleotide of claim 1.

4. A host cell transformed with the expression vector of claim 3.

5. A diagnostic composition for the detection of pac10 human homolog polynucleotide sequences comprising the polynucleotide of claim 2.

6. A diagnostic test for the detection of pac10 human homolog nucleic acid sequences encoding PAC10 human homolog in a sample, the test comprising the steps of:

a) combining the sample with the polynucleotide of claim 3 under conditions suitable for the formation of a nucleic acid hybridization complex between at least one of the nucleic acid sequences of the sample and the polynucleotide of claim 3; and b) detecting the hybridization complex, wherein the presence of the hybridization complex correlates with the presence of a polynucleotide encoding PAC10 human homolog in the sample.

7. The method of claim 6 wherein the nucleic acids of the sample are amplified by polymerase chain reaction prior to hybridization.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 1314 base pairs
    (B) TYPE: nucleic acid
    (C) STRANDEDNESS: single
    (D) TOPOLOGY: linear (ii) MOLECULE TYPE: cDNA (vii) IMMEDIATE SOURCE:
    (A) LIBRARY: TBLYNOT01
    (B) CLONE: 41400

(xi) SEQUENCE DESCRIPTION: SEQ ID NO:1:

```
TNCCCAAGNA GNCCATNCCT TTGGACAACN AGCGCAAATN ATTTACAGCA TCAAAATGGT      60
TGCAAATCCT GGNCAAATGG GNCTGCAAAA CAGCAGCTTT GTTGGAAGCC TTNTTTTNTA     120
ATTCCATGGC ATCAGAAGAC CCTTTAATGA GGCANATNAG TTCATCAANN ANAATNCCCC     180
TGGTGGGCAN AAGACTAACT NAGTNACCAT TGCACCCAGA CGCCTGGGTG CATCACAGCA     240
TTNCTGCATC AAAAACATCA ATGTNATNGT TNCATNCCCC TGTGAGTNAA AAATNACACT     300
CACACATGTT TTGTCACTGT NATTNCTGNA ANTNAAAACA TGCNGCNAAA ANAAAAAAAA     360
AAAAAAAAAA ACGCAGGGGN CGTNACCATG CGCKCTCGCA TCCCCAAGAT GGCGGCCGTT     420
AAGGACAGTT GTGGCAAAGG AGAAATGGCC ACAGGGAATG GGCGGCGGCT CCACCTGGGG     480
ATTCCTGAGG CCGTGTTTGT GGAAGATGTA GATTCCTTCA TGAAACAGCC TGGGAATGAG     540
ACTGCAGATA CAGTATTAAA GAAGCTGGAT GAACAGTACC AGAAGTATAA GTTTATGGAA     600
CTCAACCTTG CTCAAAAGAA AAGAAGGCTA AAAGGTCAGA TTCCTGAAAT TAAACAGACT     660
TTGGAAATTC TAAAATACAT GCAGAAGAAA AAAGAGTCCA CCAACTCAAT GGAGACCAGA     720
TTCTTGCTGG CAGATAACCT GTATTGCAAA GCTTCAGTTC CTCCTACCGA TAAAGTGTGT     780
CTGTGGTTGG GGGCTAATGT AATGCTTGAA TATGATATTG ATGAAGCTCA GGCATTGTTG     840
GAAAAGAATT TATCGACTGC CACAAAGAAT CTTGATTCCC TGGAGGAAGA CCTTGACTTT     900
CTTCGAGATC AATTTACTAC CACAGAAGTC AATATGGCCA GGGTTTATAA TTGGGATGTA     960
AAAAGAAGAA ACAAGGATGA CTCTACCAAG AACAAAGCAT AATGCTGGCA ATTAAAAATG    1020
TGGTTTAGTT TTCCAAACAT GTTATCTTAA ATACCCCTTT ATCCTTACAG GTTGACATAA    1080
CTTTGAATGT TTTAACAGCA AGAATTTTAA GAAAAGATAA ACACCATTTT ATTTATTTAT    1140
AAAAACAAAA TTAGTTTCAA ATATTTTTGA CATTGTGATT TTTTTTTCCA CATTTCTCAG    1200
CAAAGCTAAT GGTATTTTAA TCATTATTTT TGCCTGTCAT AAGGAAACTC TTAGCTGAAA    1260
TGGCCGNAAA CTGTGNGNCA TGCTATGGAA GCTGAATGNC GGACGNTAGC ACAG          1314
```

(2) INFORMATION FOR SEQ ID NO:2:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: TBLYNOT01
        (B) CLONE: 41400

(xi) SEQUENCE DESCRIPTION: SEQ ID NO:2:

```
Met Ala Thr Gly Asn Gly Arg Arg Leu His Leu Gly Ile Pro Glu Ala
 1               5                  10                  15
```

-continued

```
Val Phe Val Glu Asp Val Asp Ser Phe Met Lys Gln Pro Gly Asn Glu
            20                  25                  30

Thr Ala Asp Thr Val Leu Lys Lys Leu Asp Glu Gln Tyr Gln Lys Tyr
            35                  40                  45

Lys Phe Met Glu Leu Asn Leu Ala Gln Lys Lys Arg Arg Leu Lys Gly
    50                  55                  60

Gln Ile Pro Glu Ile Lys Gln Thr Leu Glu Ile Leu Lys Tyr Met Gln
65                  70                  75                  80

Lys Lys Lys Glu Ser Thr Asn Ser Met Glu Thr Arg Phe Leu Leu Ala
            85                  90                  95

Asp Asn Leu Tyr Cys Lys Ala Ser Val Pro Pro Thr Asp Lys Val Cys
            100                 105                 110

Leu Trp Leu Gly Ala Asn Val Met Leu Glu Tyr Asp Ile Asp Glu Ala
            115                 120                 125

Gln Ala Leu Leu Glu Lys Asn Leu Ser Thr Ala Thr Lys Asn Leu Asp
            130                 135                 140

Ser Leu Glu Glu Asp Leu Asp Phe Leu Arg Asp Gln Phe Thr Thr Thr
145                 150                 155                 160

Glu Val Asn Met Ala Arg Val Tyr Asn Trp Asp Val Lys Arg Arg Asn
                165                 170                 175

Lys Asp Asp Ser Thr Lys Asn Lys Ala
            180                 185
```